(12) United States Patent
Johnson et al.

(10) Patent No.: US 9,482,653 B2
(45) Date of Patent: *Nov. 1, 2016

(54) GAS EXCHANGE SYSTEM FLOW CONFIGURATION

(71) Applicant: LI-COR, Inc., Lincoln, NE (US)

(72) Inventors: Mark A. Johnson, Hickman, NE (US); Robert D. Eckles, Malcolm, NE (US); Dayle K. McDermitt, Lincoln, NE (US)

(73) Assignee: LI-COR, Inc., Lincoln, NE (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/542,926

(22) Filed: Nov. 17, 2014

(65) Prior Publication Data

US 2015/0068277 A1  Mar. 12, 2015

Related U.S. Application Data

(63) Continuation of application No. 13/240,613, filed on Sep. 22, 2011, now Pat. No. 8,910,506.

(60) Provisional application No. 61/385,909, filed on Sep. 23, 2010.

(51) Int. Cl.
*G01N 33/00* (2006.01)
*A01G 7/00* (2006.01)
(Continued)

(52) U.S. Cl.
CPC ............. *G01N 33/0031* (2013.01); *A01G 7/00* (2013.01); *G01F 1/05* (2013.01); *G01N 33/004* (2013.01); *G01N 33/0098* (2013.01); *G01N 21/3504* (2013.01); *G01N 2021/3513* (2013.01)

(58) Field of Classification Search
CPC .................................................. G01N 33/0031
USPC ................... 73/23.2, 863.02, 863.03, 863.31
See application file for complete search history.

(56) References Cited

U.S. PATENT DOCUMENTS

| 4,312,218 A | 1/1982 | Eckles |
| 4,768,390 A | 9/1988 | Baker et al. |
| 4,803,370 A | 2/1989 | Eckles |

(Continued)

FOREIGN PATENT DOCUMENTS

JP  55-047437 A  4/1980

OTHER PUBLICATIONS

LI-COR Biosciences LI-6400 User Manual, Making Measurements—Leaks, Using the LI-6400/LI-6400XT, Version 6, pp. 4-43-4-48. (Appendix A to Provisional Patent Applications from which the subject application claims priority).

(Continued)

*Primary Examiner* — Laura Martin
*Assistant Examiner* — Alex Devito
(74) *Attorney, Agent, or Firm* — Leydig, Voit & Mayer, LTD; Gerald T. Gray

(57) ABSTRACT

Active compensation designs to offset the impact of gas diffusion sources and sinks in a photosynthesis and transpiration measurement system are disclosed. A sensor head for use in a gas exchange analysis system includes an active, piezoelectric flow splitting device for splitting a flow between a sample chamber and bypass pathway. The active flow splitting device is controlled by feedback from a downstream flow meter. A continuous measurement system for rapidly and accurately surveying large numbers of samples is described.

13 Claims, 7 Drawing Sheets

(51) Int. Cl.
*G01F 1/05* (2006.01)
*G01N 21/3504* (2014.01)

(56) References Cited

U.S. PATENT DOCUMENTS

| | | | |
|---|---|---|---|
| 5,077,469 | A | 12/1991 | Fabinski et al. |
| 5,220,402 | A | 6/1993 | Harvey |
| 5,332,901 | A | 7/1994 | Eckles et al. |
| 5,340,987 | A | 8/1994 | Eckles et al. |
| 5,457,320 | A * | 10/1995 | Eckles et al. ............... 250/345 |
| 5,793,044 | A | 8/1998 | Mace et al. |
| 5,932,877 | A | 8/1999 | Braig et al. |
| 6,317,212 | B1 | 11/2001 | Eckles et al. |
| 7,063,667 | B1 | 6/2006 | Ben-Oren et al. |
| 7,323,687 | B2 | 1/2008 | Nanko et al. |
| 7,748,253 | B2 | 7/2010 | Furtaw et al. |
| 2003/0214372 | A1* | 11/2003 | Miura et al. .................. 333/195 |
| 2007/0246653 | A1 | 10/2007 | Zhou |
| 2008/0277586 | A1 | 11/2008 | Cardinale |
| 2008/0304979 | A1* | 12/2008 | Lucas ........................... 417/327 |
| 2010/0028977 | A1 | 2/2010 | Ng et al. |
| 2010/0110437 | A1 | 5/2010 | Furtaw et al. |
| 2010/0262382 | A1 | 10/2010 | Lighton |
| 2012/0074324 | A1 | 3/2012 | Genty et al. |
| 2012/0074325 | A1 | 3/2012 | Johnson et al. |

OTHER PUBLICATIONS 6400-22L Lighted Conifer Chamber—Li-Cor Environmental NewsLine (Jul. 2009), http://www.licor.com/env/newsline/2009/07/6400-22I.

Christopher B. Field, J. Timothy Ball and Joseph A. Berry, "Photosynthesis: principles and field techniques".

Robert W. Pearcy and Jeffrey R. Seemann, "Photosynthetic Indcution State of Leaves in a Soybean Canopy in Relation to light Regulation of Ribulose-1-5- Bisphosphate Carboxylase and Stomatal Conductance," (Jun. 11, 1990), Plant Physiol., vol. 94, pp. 628-633.

Joanna C. Rooke, Christophe Meuneir, Alexandre Leonard, and Bao-Lian Sue, "Energy from photobioreactors: Bioencapsulation of photosynthetically active molecules, organelles, and whole cells within biologically inert matrices," (2008), Pure Appl. Chem., vol. 80, No. 11, pp. 2345-2376.

Using the Li-6400/L1-6400XT Version 6', Li-Cor Bioscience, Inc., Publication No. 9806-122, (Jul. 31, 1998).

Using the Li-6400/L1-6400XT Version 6', Li-Cor Bioscience, Inc., Publication No. 9806-122, (Nov. 2008).

International Search Report and Written Opinion for PCT/US2011/052724 issued Apr. 23, 2012.

International Search Report and Written Opinion for PCT/US2011/052821 issued Apr. 24, 2012.

U.S. Appl. No. 13/240,613, filed Sep. 22, 2011.

* cited by examiner

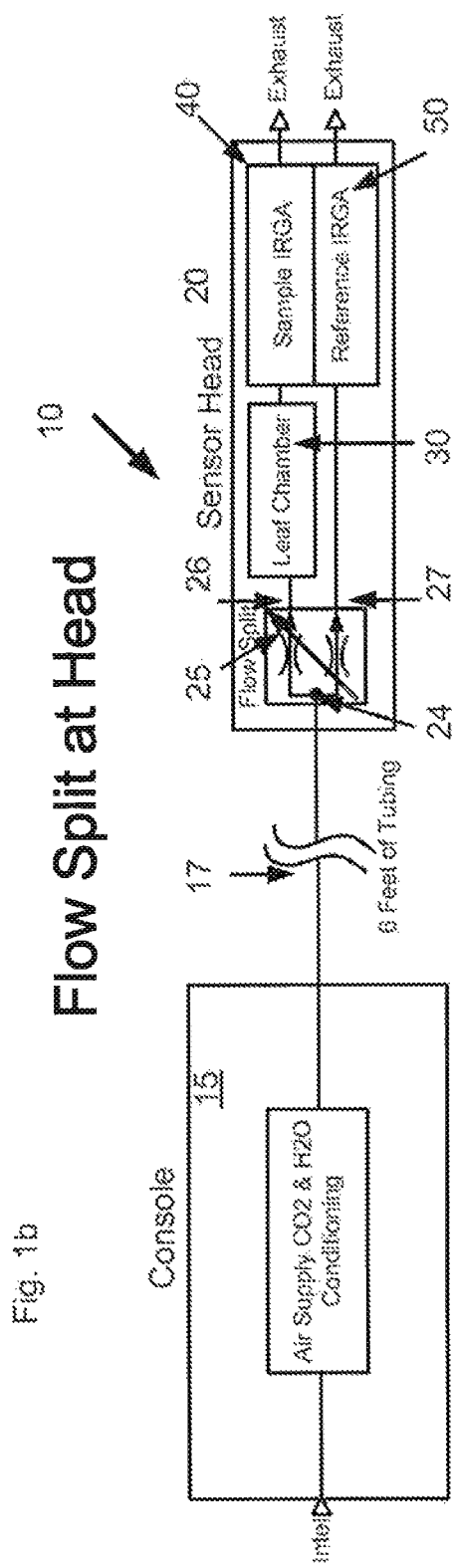

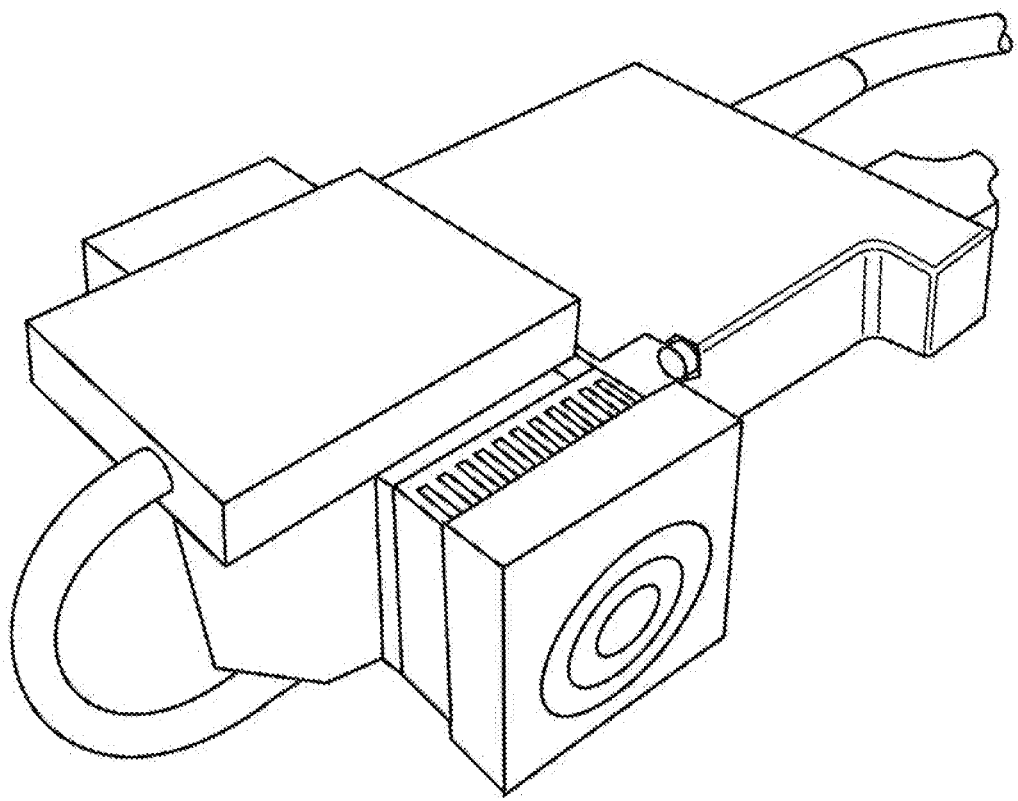
FIG. 2 Sensor head with leaf chamber blocked off

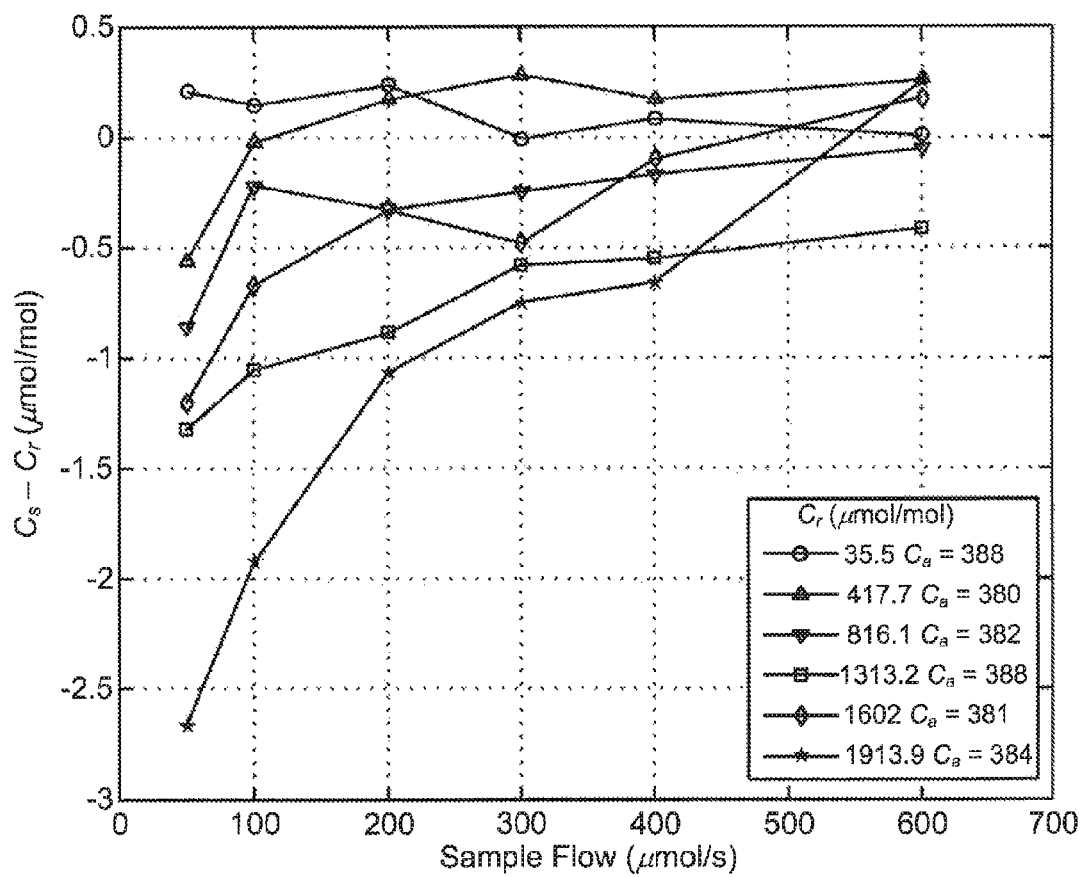
FIG. 3 CO2 Diffusion with leaf chamber sealed off. Flow is split at console.
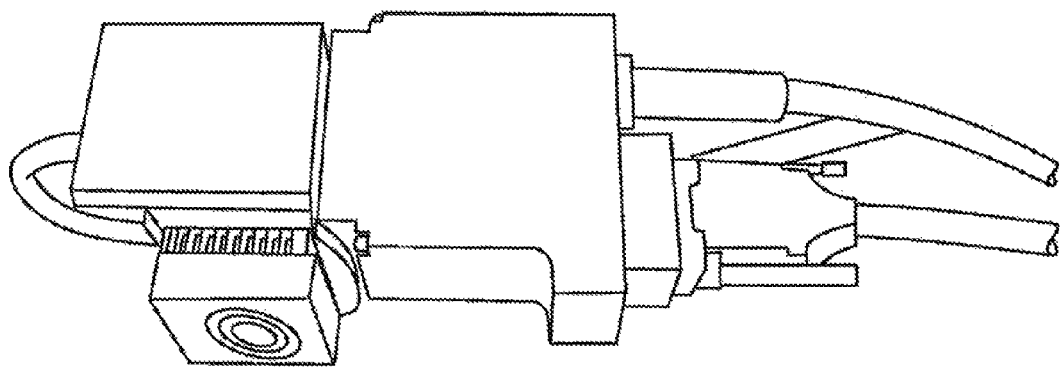
FIG. 4 Sensor head with flow split at the head

GAS EXCHANGE SYSTEM FLOW CONFIGURATION

CROSS-REFERENCES TO RELATED APPLICATIONS

This application claims the benefit of U.S. Non-Provisional application Ser. No. 13/240,613, and Provisional Application No. 61/385,909, filed on Sep. 23, 2010, the disclosure of which is incorporated herein by reference in its entirety.

This application is related to U.S. application Ser. No. 13/149,709, filed May 31, 2011, which is a continuation-in-part of U.S. application Ser. No. 12/889,289, filed on Sep. 23, 2010, the disclosures of which are incorporated herein by reference in their entireties.

STATEMENT AS TO RIGHTS TO INVENTIONS MADE UNDER FEDERALLY SPONSORED RESEARCH OR DEVELOPMENT

Not Applicable

BACKGROUND

The present invention relates generally to gas exchange measurement systems, and more particularly to open photosynthesis measurement systems having an optimized flow configuration to minimize errors resulting from gas diffusion.

Systems for measuring plant photosynthesis and transpiration rates can be categorized as open or closed systems. For open systems, the leaf or plant is enclosed in a chamber, and an air stream is passed continuously through the chamber. $CO_2$ and $H_2O$ concentrations of chamber influent and effluent are measured, and the difference between influent and effluent concentration is calculated. This difference is used, along with the mass flow rate, to calculate photosynthesis ($CO_2$) and transpiration ($H_2O$) rates. For closed systems, the leaf or plant is enclosed in a chamber that is not supplied with fresh air. The concentrations of $CO_2$ and $H_2O$ are continuously monitored within the chamber. The rate of change of this concentration, along with the chamber volume, is used to calculate photosynthesis ($CO_2$) and transpiration ($H_2O$) rates.

In both open and closed systems, it is important that the leaf or plant be the only source or sink of both $CO_2$ and $H_2O$. $CO_2$ or $H_2O$ concentration changes not caused by the plant are a measurement error. These errors can be empirically compensated, for example as described in the LI-COR Biosciences LI-6400 User Manual (pp. 4-43 thru 4-48). Some instrument users may not understand the significance of these corrections, and neglect them.

Both open and closed systems contain a circuit of pneumatic components (e.g., pumps, valves, chambers, tubing, analyzers, etc.). When $CO_2$ and $H_2O$ concentrations are dynamically changing, sorption on these components can provide an apparent $CO_2$ or $H_2O$ source and/or sink. Under steady-state conditions, sorption is not an active source or sink, and parasitic $CO_2$ and $H_2O$ sources and/or sinks can be attributed to bulk leaks and diffusion.

Bulk leaks are driven by pressure differentials between the system and the ambient environment. Proper system design and construction, along with inherently low operating pressures, generally minimize parasitic sources and sinks due to bulk leaks. Diffusion is driven by constituent gas ($CO_2$ and $H_2O$) concentration gradients between the system and ambient environment. Any time constituent gas concentrations inside the system are significantly different than ambient conditions, the diffusion potential increases. Metals, in nearly any practical working thickness, generally provide an outstanding diffusion barrier to gases. Practically, however, nonmetallic materials are always required. For example, to provide a seal between metallic materials, gaskets and O-rings are used Flexible tubing which connects the sensor head to other system components is an example of functional capabilities which cannot be reasonably achieved with metals.

In open photosynthesis systems, a conditioned air stream is typically split into two streams. FIG. 1a illustrates the flow path in such an open system where the flow is split at the console, remote from the sensor head, and flows to the sensor head via two separate paths. The first flow path (known as reference) passes through a gas analyzer (e.g., Infra-Red Gas Analyzer or IRGA) which measures constituent gas concentrations ($CO_2$ and $H_2O$). The second flow path (known as sample) passes through a sample chamber (leaf chamber) in which gas exchange occurs. This second sample flow path exits the chamber and enters a second gas analyzer (e.g., IRGA). The difference between the sample and reference gas concentrations is used to calculate photosynthesis ($CO_2$) and transpiration ($H_2O$). As photosynthesis and transpiration measurements are based on concentration differences in these two gas streams, the accuracy in measuring the difference is more critical than measuring the absolute concentration of either. Diffusive parasitic sources and/or sinks present in the tubing, connectors, and fittings that supply the head with the sample and reference gas streams can compromise measurement accuracy.

In practice, it is nearly impossible to fully eliminate parasitic sources and sinks due to diffusion. Therefore it is desirable to provide systems and methods that minimize the impact of diffusion and that help overcome the above and other problems.

BRIEF SUMMARY

The present invention provides systems and methods for measuring photosynthesis and transpiration rates.

Embodiments of the invention provide system flow path designs that help minimize the impact of diffusion. By reducing the magnitude of parasitic source and sinks, lower rates of photosynthesis and transpiration can be more accurately measured, e.g., without the need for extensive empirical compensation. Other embodiments provide systems and methods for performing survey measurements of gas concentration and also gas analyzers having piezoresistive or other active flow splitting devices that variably split a received gas flow to two gas outlet ports or channels.

According to one embodiment, a sensor head for use in a gas exchange measurement system is provided. The sensor head typically includes a sample chamber defining a measurement volume for analysis of a sample, the sample chamber having an inlet and an outlet, and a flow splitting mechanism located proximal to the sample chamber, the mechanism configured to split a gas flow received at an input port from a remote source to a first output port and to a second output port, wherein the first output port is coupled with the inlet of the sample chamber. The sensor head also typically includes a first gas analyzer coupled with the outlet of the sample chamber and configured to measure a concentration of one or more gases, and a second gas analyzer coupled with the second output port of the flow splitting mechanism and configured to measure a concentration of the one or more gases. Advantageously, gas diffusion sources and sinks, which differentially affect gas concentrations, are reduced due to the proximity of the flow splitting mechanism with the sample chamber and gas analyzers. This advantageously reduces measurement error associated with or attributable to gas diffusion sources and sinks. The proximity advantage derives from minimizing the joints, gaskets, fittings, tubing lengths, and materials all prone or susceptible to gas diffusion. In certain aspects, the one or more gases measured by the first and second gas analyzers includes CO2 or H2O.

According to another embodiment, a method is provided for measuring a gas concentration differential in a gas exchange analysis system having a sensor head having a sample chamber defining a measurement volume for sample analysis, the sample chamber having an inlet and an outlet, and a flow splitting mechanism located proximal to the sample chamber. The method includes splitting a gas flow received from a remote source at an input port of the flow splitting mechanism to a first output port and to a second output port, wherein the first output port is coupled with the inlet of the sample chamber, measuring a concentration of one or more gases exiting the sample chamber using a first gas analyzer, and measuring a concentration of the one or more gases exiting the second output port of the flow splitting mechanism using a second gas analyzer. The method also includes determining a concentration differential of the one or more gases based on the first concentration and the second concentration, whereby measurement errors associated with diffusion sources and sinks of said gas are reduced due to the proximity of the flow splitting mechanism to the sample chamber and gas analyzers. In certain aspects, the measured gases include $CO_2$ or $H_2O$.

According to yet another embodiment, a device is provided for variably splitting the flow of gas in a sensor head of a gas exchange analysis system. The device typically includes an input port, a first output port, a second output port and a flow splitting mechanism, the device being located proximal to a sample analysis chamber having a measurement volume, and gas analyzers. The flow splitting mechanism is typically configured to variably split a gas flow received at the input port from a remote source to the first output port and to the second output port, wherein the first output port is coupled via a flow path to an inlet of the sample analysis chamber. The flow volume created by the measurement volume and the flow path is sufficiently small such as to reduce the time required to reach a steady state of gas concentrations in the flow volume when a flow ratio to the flow path is adjusted in the flow splitting mechanism. In certain aspects, the flow splitting mechanism is configured to variably adjust the flow ratio such that the gas flow is about 0% to 100% to the first output port and the remaining 100% to 0% to the second output port.

According to a further embodiment, a sensor head for use in a gas exchange analysis system is provided that typically includes a sample chamber defining a measurement volume for analysis of a sample, the sample chamber having an inlet and an outlet, and a piezoresistive flow splitting device located proximal to the sample chamber, the device configured to variably split a gas flow received at an input port to a first output port and to a second output port, wherein the first output port is coupled with the inlet of the sample chamber. The sensor head also typically includes a first gas analyzer coupled with the outlet of the sample chamber and configured to measure a concentration of a gas, a second gas analyzer coupled with the second output port and configured to measure a concentration of said gas, and a flow meter coupled between the first output port and the inlet of the sample chamber or between the second output port and the second gas analyzer, the flow meter being adapted to measure a flow rate. The sensor head further typically includes a feedback control circuit adapted to control the piezoresistive flow splitting device to adjust a ratio of gas flow to the first and second output ports responsive to a flow rate signal from the flow meter. En certain aspects, the piezoresistive flow splitting device is configured to variably adjust the flow ratio such that the gas flow is between about 0% to 100% to the first output port and concomitantly between about 100% to 0% to the second output port.

According to yet a further embodiment, a method is provided for measuring a concentration of a gas in a gas exchange analysis system having a sample chamber defining a measurement volume for analysis of a sample, the sample chamber having an inlet port coupled with a gas source and an outlet port. The method typically includes measuring a first concentration of a gas at the input port at each of a plurality of times, measuring a second concentration of said gas at the output port at each of said plurality of times, and thereafter determining at each of said plurality of times a concentration differential between the first measured concentration and the second measured concentration and integrating the concentration differential over time.

According to yet another embodiment, an open-path gas exchange analysis system is provided that includes an enclosed sample chamber defining a measurement volume for analysis of a sample, with the sample chamber having a gas inlet port coupled with a gas source and a gas outlet port. The system also includes a first gas analyzer configured to measure a first concentration of a gas entering the gas inlet port, a second gas analyzer configured to measure a second concentration of said gas exiting the gas outlet port at the plurality of times, and a processing module configured to determine at each of the plurality of times a concentration differential between the first measured concentration and the second measured concentration, and to integrate the concentration differential over time. In certain aspects, the measured gas includes $CO_2$ or $H_2O$.

According to another embodiment, a sensor head is provided for use in a gas exchange analysis system, the sensor head including an active flow splitting device having a first output port and a second output port, the active flow splitting device configured to variably split an incoming gas flow between the first and second output ports, a sample chamber having an inlet and an outlet, the inlet coupled with the first output port of the active flow splitting device, a first gas analyzer coupled with the outlet of the sample chamber and configured to measure a concentration of a gas, a second gas analyzer coupled with the second output port of the active flow splitting device and configured to measure a concentration of said gas, a flow meter coupled between the first output port of the active flow splitting device and the inlet of the sample chamber or between the second output port of the active flow splitting device and the second gas analyzer, the flow meter configured to measure a flow rate, and a feedback control circuit adapted to control the active flow splitting device to adjust the incoming gas flow to the first and second output ports responsive to a flow rate signal from the flow meter.

According to another embodiment, a method of measuring gas exchange is disclosed. The method includes flowing gas through an active flow splitting device having a first output port and a second output port, the active flow splitting device configured to variably split an incoming gas flow between the first and second output ports, flowing gas from the first output port of the active flow splitting device to a sample chamber having an inlet and an outlet, determining a concentration of gas flowing from the outlet of the sample chamber, determining a concentration of gas flowing from the second output port of the active flow splitting device, measuring a flow rate between the first output port of the active flow splitting device and the inlet of the sample chamber or between the second output port of the active flow splitting device and the second gas analyzer, and sending feedback to the active flow splitting device based on the measured flow rate.

Reference to the remaining portions of the specification, including the drawings and claims, will realize other features and advantages of the present invention. Further features and advantages of the present invention, as well as the structure and operation of various embodiments of the present invention, are described in detail below with respect to the accompanying drawings. In the drawings, like reference numbers indicate identical or functionally similar elements.

BRIEF DESCRIPTION OF THE DRAWINGS

FIG. 1b illustrates a flow path in a photosynthesis measurement system cording to one embodiment.

FIG. 2 illustrates a sensor head with a leaf chamber blocked off.

FIG. 3 shows the results of the experiment with the configuration in FIG. 2, using the experimental protocol outlined in the LI-COR Biosciences LI-6400 User Manual (pp 4-43 through 4-48).

FIG. 4 illustrates a different perspective view of the sensor head of FIG. 2.

DETAILED DESCRIPTION

The present invention provides systems and methods for measuring photosynthesis and transpiration rates, systems and methods for performing survey measurements of gas concentration and also gas analyzers having piezoresistive or other active flow splitting devices that variably split a received gas flow to two gas outlet ports or channels and can be controlled precisely through feedback loops.

"Active" devices include those that can be controlled electronically by a computer, controller, or other machine. Active devices often can be adjusted in real-time automatically without intervention by a human operator.

Technical advantages of using a piezoelectric flow splitter include that they can operate with very low power consumption, which is beneficial for battery-powered instruments. Physical size of piezoelectric flow splitters is relatively small, and geometries of piezo actuators are favorable for small instruments.

A closed loop feedback controller for a flow splitter has been shown to have superior performance for gas exchange analysis systems that measure delicate photosynthesis affects of real-world plants. The flow on one side of a flow split into a leaf measurement chamber should be precisely known and controlled in order for evapotransporation to be accurately measured within the chamber. Flow rate is one of the parameters of a leaf photosynthesis measurement. An flow splitter without feedback (i.e., open loop) might drift because conditions in the leaf chamber might change. The changing conditions can include temperature, partial pressures of certain gases, etc. These changes can include a pressure change that could affect flow rate through the chamber.

In some embodiments, it is desirable to adjust the amount of flow going into the leaf measurement chamber to accommodate different measurement conditions. However, since the amount of flow before the flow split is usually constant, changing the split ratio has been found to be a good way to regulate and control the flow to the sample chamber. One can control the flow into the sample chamber because it should be precisely known and regulated. Excess flow that is left over can be used for the reference path. Having the flow splitter located very close to or otherwise proximate to the chamber paths has been found to largely eliminate adsorption effects of the chamber, hose, and fitting walls.

Figure 1A:
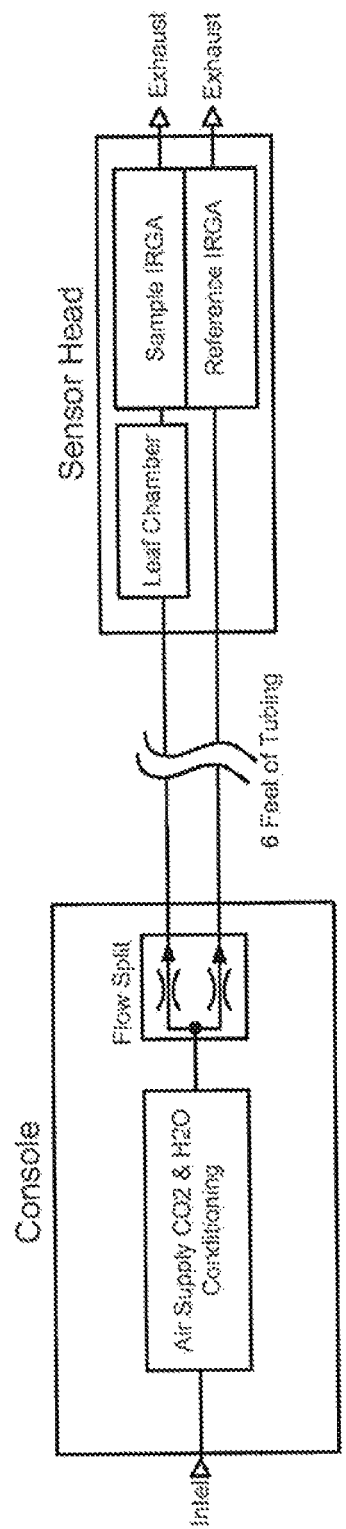
FIG. 1a illustrates the flow path in a prior photosynthesis measurement system where the flow is split at the console, remote from the sensor head.

FIG. 1b illustrates a flow path in a gas exchange measurement system 10 according to one embodiment. Gas exchange measurement system 10 in one embodiment includes a console 15 and a sensor head 20 remote from console 15. Console 15 typically includes, or is connected with, one or more gas sources and gas conditioning equipment. For example, in the context of photosynthesis and transpiration measurements, gas sources would include reservoirs of $CO_2$ and $H_2O$, and conditioning equipment for conditioning each gas concentration. A flow path 17 connecting console 15 with sensor head 20 typically includes flexible tubing and connectors. Flow path 17 provides a single stream or gas flow path to flow splitting mechanism 25 in sensor head 20. Flow splitting mechanism 25 receives a stream of gas from console 15 and splits the flow into two separate flow paths as will be described in more detail below. One stream is provided to the chamber 30 (e.g., sample stream) and the other stream (e.g., reference stream) is provided to a reference gas analyzer 50. A second gas analyzer 40 receives and analyzes gas from chamber 30. Reference gas analyzer 50 and second gas analyzer 40 might each include an Infra-Red Gas Analyzer (IRGA), as is known in the art, or other gas analyzer.

It is desirable that flow path lengths and the number of connections downstream of the flow split device 25 be minimized to reduce parasitic sources and sinks which differentially affect concentrations in the two flow paths. Hence, according to one embodiment, the flow path is split in the sensor head proximal to the sample chamber. The majority of parasitic sources and sinks, which are located upstream of the sensor head in FIG. 1b, affect only a single air stream (flow path 17) when the flow is split at the sensor head 20. Parasitic sources and sinks which impact the sample and reference streams independently are advantageously minimized.

It is desirable that for a certain flow rate, through either the reference or sample path, less than a certain amount of diffusion occurs. As one example, for embodiments of the present invention, it is desirable that 0.1 µmole/mole (PPM) or less of CO2 concentration change occur at a flow rate of about 50 µmol/sec in the sample leg. This corresponds to an effective diffusion rate of $CO^2$ of 5 µmoles/sec. For a given diffusion source/sink rate, as the flow rate increases, the concentration change due to the diffusion source/sink has a smaller concentration effect; concomitantly, a given diffusion source/sink has a greater effect on concentration at a smaller flow rate. Hence, as above, it is desirable to minimize the flow path lengths having diffusion-susceptible material and components to reduce or minimize parasitic sources and sinks of gases. One way to do this is to minimize the flow path length itself. An additional, or alternate, way is to reduce or minimize components of the flow path that are diffusion-susceptible. In practice, however, certain diffusion-susceptible materials and components are used for cost and efficiency reasons. Therefore, according to one embodiment, the flow is split as close to the sample chamber and gas analyzers as possible. In certain aspects, the flow splitting mechanism 25 is located such that a minimal amount of flow path having components or surface areas exposed or susceptible to diffusion exists between the flow splitting device 25 and the sample chamber 30. The desired length of the flow path is generally a function of the flow rate and the diffusion susceptible material or components making up the flow path; for example, for metal tubing, the flow path can be significantly longer than for plastic or other diffusion-susceptible components. For example, in certain aspects, a flow path having 12" or less of diffusion-susceptible tubing and/or other components is desirable to couple the flow splitting mechanism 25 with the sample chamber 30 to provide a gas stream flow path from the splitting mechanism. In other aspects, less than about 6", or 4" or 2" or even 1" or less of such diffusion-susceptible flow path exists between the flow splitting device 25 and the sample chamber 30.

Similarly, in certain aspects, the flow splitting mechanism is located in the sensor 30 head such that less than about 12" of such diffusion-susceptible flow path exists between the flow splitting device 25 and the reference gas analyzer 50. In other aspects, the flow splitting mechanism is located such that less than about 6", or 4" or 2" or even 1" or less of such flow path exists between the flow splitting device 25 and the reference gas analyzer 50. It is also desirable that that flow path length between the sample chamber 30 and sample gas analyzer 40 be minimized. One skilled in the art will appreciate that the diffusion-susceptible flow path from the flow splitting mechanism 25 to the reference gas analyzer 50 can be roughly the same length as the diffusion-susceptible flow path from the splitting mechanism 25 through the sample chamber 30 to the sample gas analyzer 40. Alternately, the two diffusion-S susceptible flow paths can be different lengths as desired.

Experiments using the LI-COR Biosciences LI-6400 have verified that diffusion through flexible tubing, gaskets, and pneumatic connectors is a significant and quantifiable issue. In one experiment, to eliminate diffusion sources/sinks from the leaf chamber, the chamber was removed from the LI-6400 head (see, e.g., FIG. 1a) and was replaced with an aluminum block and a vinyl gasket as shown in FIG. 2. FIG. 4 illustrates a different perspective view of the sensor head of FIG. 2. FIG. 3 shows the results of the experiment with the configuration in FIG. 2, using the experimental protocol outlined in the LI-6400 User Manual (pp 4-43 through 4-48). FIG. 3 shows there are significant differences between the sample (Cs) and reference (Cr) concentrations of $CO_2$ in the absence of a leaf The differences shown in FIG. 3 are due exclusively to parasitic sources and sinks of $CO_2$. As there were no known bulk leaks during the experiment, the differences shown in FIG. 3 are dominated by diffusion. The magnitude of the concentration difference is largest at low flow rates and at large $CO_2$ concentrations (relative to ambient Ca).

FIG. 3 demonstrates that the diffusive parasitic sources and/or sinks can be attributed to system components other than the leaf chamber and leaf gaskets. The diffusion source and/or sink must be present in the tubing, pneumatic connectors and fittings that supply the head with the sample and reference gas streams.

A difference in sample and reference flow rates causes a difference in concentrations even if the diffusive rates are approximately equal. FIG. 3 shows that at low sample flow rates, and a given stream concentration, the concentration difference (Cs–Cr) is more pronounced than at higher sample flow rates. For example, at a nominal concentration of 1913.9 PPM of $CO_2$, (Cs–Cr) is approximately –2.6 PPM at the lowest flow rate. Ambient $CO_2$ concentration is approximately 384 PPM. Under these flow conditions, the sample flow rate is much lower than the reference flow rate, and diffusion reduces the concentration of the sample much more than the reference, resulting in the negative value of (Cs–Cr). The reduction occurs because of diffusive parasitic sinks, whereas at a nominal concentration of 35.5 PPM (below ambient Ca of 388 PPM), the values of (Cs–Cr) are positive, and parasitic diffusion acts as a source.

Splitting the flow at the sensor head, according to one embodiment, reduces the number of components (e.g., tubing, connectors and fittings), and the pneumatic path length, subjected to parasitic $CO_2$ sources and/or sinks, thereby reducing the magnitude of the difference in (Cs–Cr) due to systematic issues. The advent of smaller pneumatic components, including MEMS-based mass flow meters, has enabled a practical implementation of splitting the flow path in the sensor head. One useful flow meter is produced by Omron, e.g., part number D6F-02A3.

In one embodiment, the flow splitting mechanism 25 is configured to variably split the flow of gas in the sensor head. In particular, the flow splitting mechanism is configured to variably split a gas flow received at the input port 24 from a remote source (console 15) to a first output port and to the second output port as shown in FIG. 1b. The second output port is coupled via a flow path 27 with an inlet of the second IRGA 50. The first output port is coupled via a flow path 26 with an inlet of the sample analysis chamber 30. A flow volume, including the measurement volume in the sample chamber 30 and the flow path, is sufficiently small such as to reduce the time required to reach a steady state of gas concentrations in the flow volume when a flow ratio to the flow path is adjusted in the flow splitting mechanism. For example, the measurement volume might be on the order of 1 mL to 10 mL to about 1000 mL, such that the flow path including the flow volume between the flow splitting device and the sample IRGA 40 might be smaller than, or on the order of, about 20 mL to about 1000 mL. In certain aspects, the flow splitting mechanism is configured to adjust the flow ratio such that the gas flow can be controllably, and continuously, varied to provide a flow range of between about 0% to 100% to the first output port and the remaining 100% to 0% to the second output port. For example, the flow splitting mechanism can be controlled via a control signal to split the flow 25% to one of the first port or second output port and 75% to the other output port, or 50% to one output port and 50% to the other output port.

Figure 5:
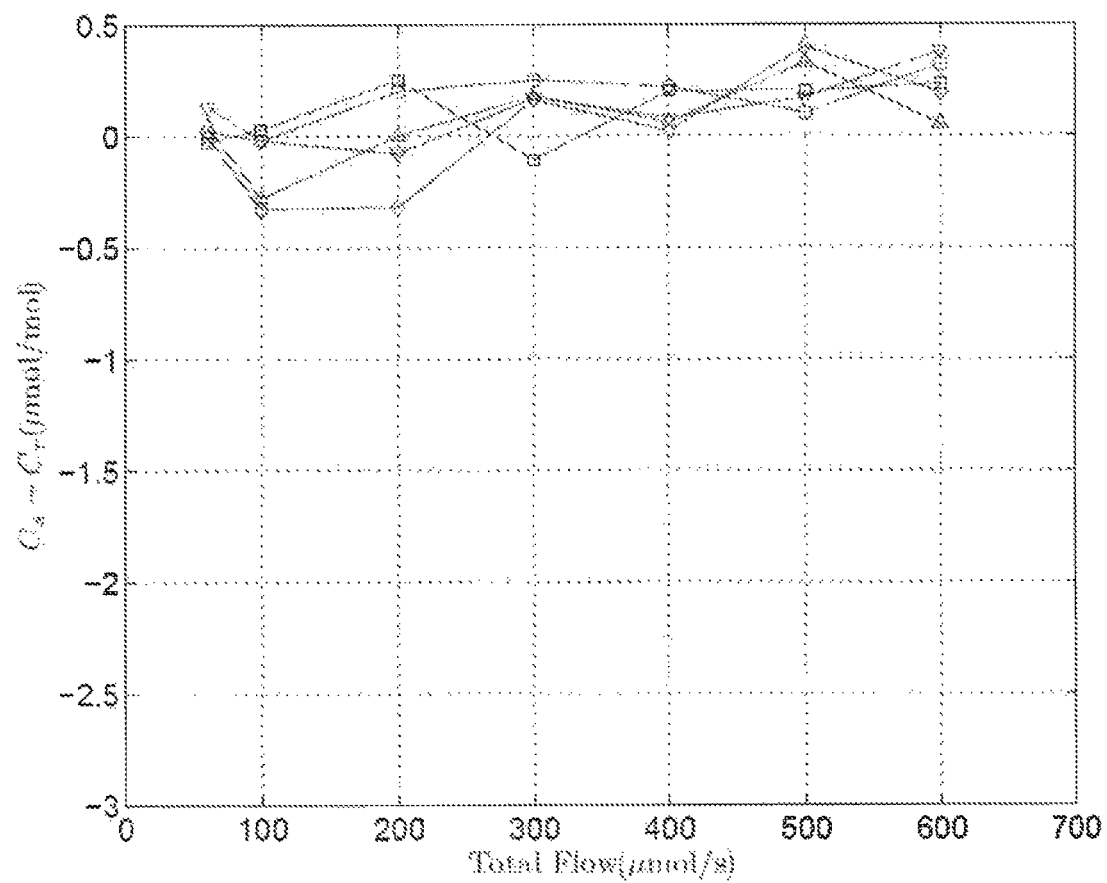
FIGS. 5 and 6 illustrate results of an experiment that shows a significant reduction in the $CO_2$ concentration difference (Cs–Cr) between the sample and reference.
Figure 6:
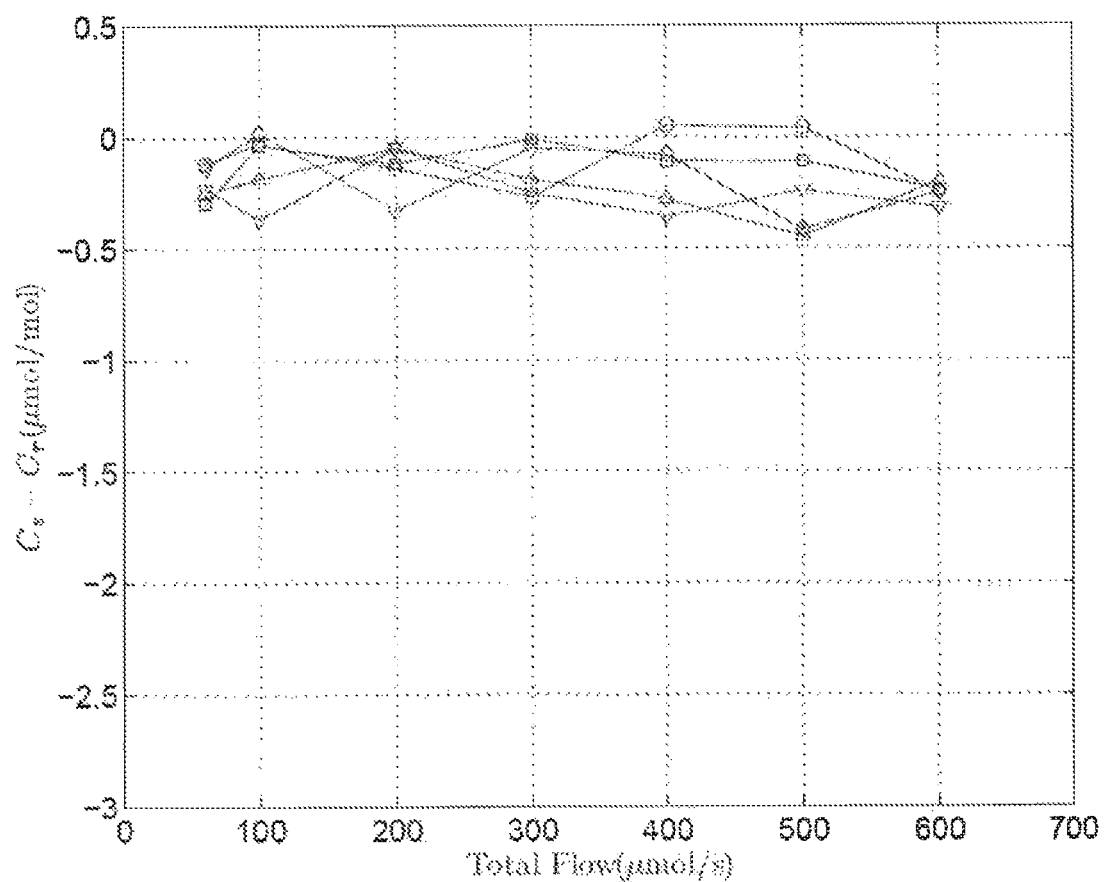

Experiments were conducted with an approximate 50%-50% flow split (50% of flow to reference, 50% to sample) and a 75%-25% flow split (75% to reference, 25% to sample) at the head of a LI-6400 instrument. The results (FIG. 5 and FIG. 6) show a significant reduction in the $CO_2$ concentration difference (Cs–Cr) between the sample and reference. The $CO_2$ concentration inside the IRGA was roughly 1940 tmol/mol for the experiments of FIG. 5 and FIG. 6. Comparing FIG. 3 (Cr=1913.9 mol/mol) with FIG.

6 demonstrates that splitting the flow at the head can reduce diffusion effects by nearly an order-of-magnitude.

In one embodiment, flow splitting mechanism 25 includes a piezoresistive flow splitting device is provided for use in a sensor head of a gas exchange analysis system. The device is configured to variably split a gas flow received at an input port 24 to a first output port 26 and to a second output port 27, wherein the first output port is coupled with the inlet of a sample chamber 30. Gas analyzer 40 is coupled with the outlet of the sample chamber and is configured to measure a concentration of a gas in the gas flow exiting the sample chamber, and gas analyzer 50 is coupled with the second output port and configured to measure a concentration of the gas in the gas flow exiting the flow splitting device. Also included is a flow meter coupled between the output port 26 and the inlet of the sample chamber 30 or between the output port 27 and the gas analyzer 50, the flow meter being adapted to measure a flow rate in the flow path, and a feedback control circuit adapted to control the piezoresistive flow splitting device to adjust a ratio of gas flow to the first and second output ports responsive to a flow rate signal from the flow meter.

In certain aspects, the piezoresistive flow splitting device includes a piezoresistive actuator having a first end secured within the device and a second end located proximal both the output port 26 and the output port 27, and electrical contacts for providing a control potential to the actuator to control the position of the second end relative to the output ports and thereby control the flow ratio to the output ports. For example, in certain aspects, an applied control potential controls the second end to adjust the position of the second end relative to the output ports such as to controllably adjust a flow ratio of between about 0% to 100% to the output port 26 and concomitantly between about 100% to 0% to the output port 27. In one embodiment, the actuator includes a metal strip coated on both sides with a piezo-bender material. In certain aspects, the piezo-bender material includes lithium tantalite or other piezo-resistive material known to one skilled in the art.

Figure 7:
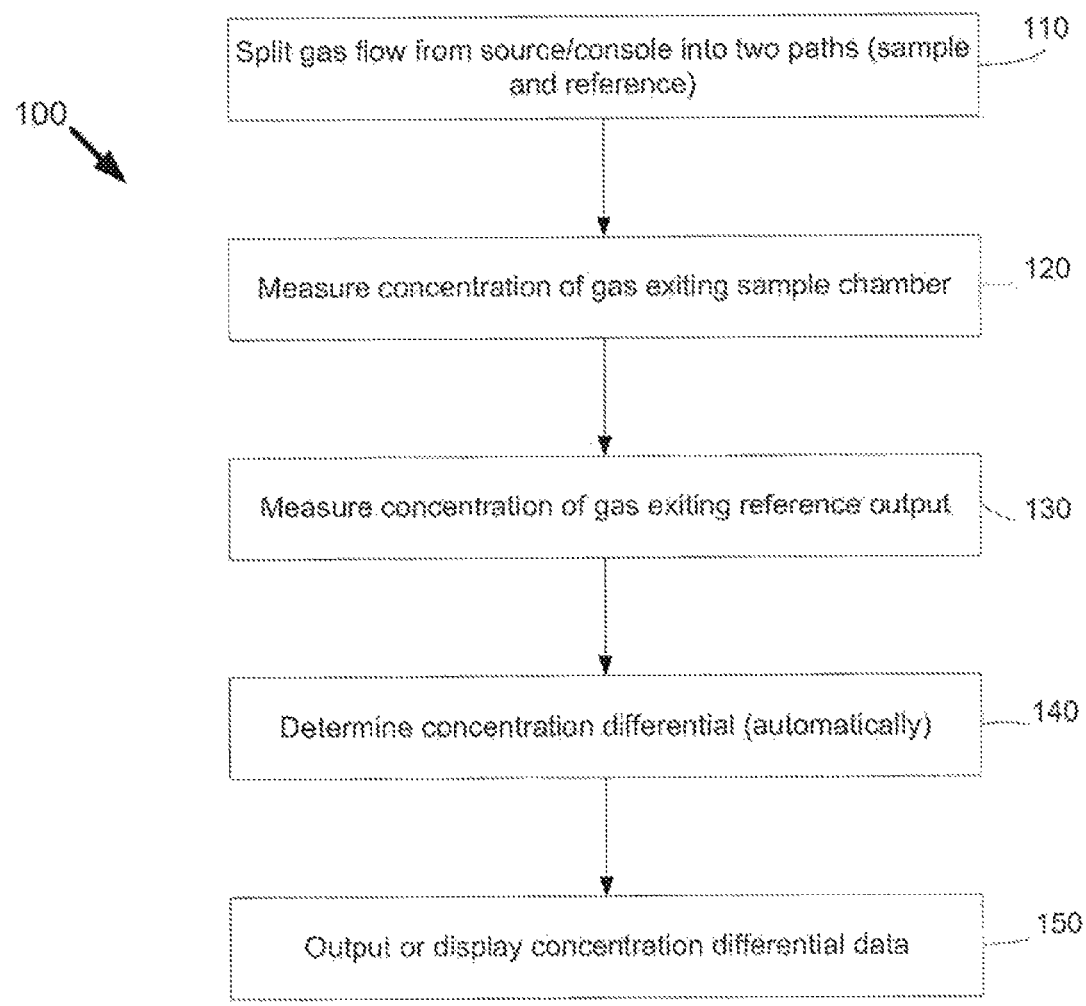
FIG. 7 illustrates a method of measuring a concentration differential of a gas in a gas exchange analysis system according to one embodiment.

FIG. 7 illustrates a method 100 of measuring a concentration differential of a gas in a gas exchange analysis system according to one embodiment. The gas exchange analysis system includes a sensor head having a flow splitting mechanism located proximal to a sample chamber that defines a measurement volume for analysis of a sample. The sample chamber includes an inlet and an outlet, with the inlet being connected, in close proximity, with an output port of the flow splitting device. The outlet is connected, also preferably in close proximity, with a gas analyzer such as an IRGA. In step 110, a gas flow received from a remote source at an input port of the flow splitting mechanism is controllably split to a first output port and to a second output port, with the first output port being coupled with the inlet of the sample chamber. In step 120, a first concentration of one or more gases exiting the sample chamber is measured using a first gas analyzer (e.g., gas analyzer 40) fluidly coupled with an output of the sample chamber. In step 130, a second concentration of the one ore more gases exiting the second output port is measured using a second gas analyzer (e.g., gas analyzer 50) fluidly coupled with the second output port of the flow splitting device. In step 140, a concentration differential of the one or more gases is determined based on the first measured concentration and the second measured concentration. Step 140 can be performed using a processor or computer system that is integrated in the sensor head and/or in the console of the gas analysis system and/or in a remote computer system that is communicably coupled with the gas analysis system. In step 150, the concentration differential is output, e.g., displayed on a monitor or other output device, printed, stored, or otherwise provided to another computer system or device. Advantageously, measurement error associated with diffusion sources and sinks of the gas are reduced due to the proximity of the flow splitting mechanism with the sample chamber.

In another embodiment, an open-path gas exchange analysis system includes a first gas analyzer (e.g., IRGA) configured to measure a first concentration of a gas entering the gas inlet port of the sample chamber at a plurality of times and a second gas analyzer (e.g., IRGA) configured to measure a second concentration of the gas exiting the gas outlet port of the sample chamber at the plurality of times. The enclosed sample chamber defines a measurement volume for analysis of a sample, where the gas inlet port of the sample chamber is coupled with a gas source. The system also includes a processing module, communicably coupled with the first and second gas analyzers, configured to determine at each of the plurality of times a concentration differential between the first measured concentration and the second measured concentration, and to integrate the concentration differential over time. The results (data) can be output, displayed or otherwise provided to another system or device for further manipulation. According to one embodiment, a method of measuring a concentration of a gas in such a gas exchange analysis system includes measuring a first concentration of a gas at the input port of the sample chamber at each of a plurality of times, measuring a second concentration of the gas at the output port of the sample chamber at each of said plurality of times, and thereafter determining at each of the plurality of times a concentration differential between the first measured concentration and the second measured concentration, and integrating the concentration differential over time. In certain aspects, the gas includes $CO_2$ and/or $H_2O$.

While the invention has been described by way of example and in terms of specific embodiments, it is to be understood that the invention is not limited to the disclosed embodiments. To the contrary, it is intended to cover various modifications and similar arrangements as would be apparent to those skilled in the art. Therefore, the scope of the appended claims should be accorded the broadest interpretation so as to encompass all such modifications and similar arrangements.

What is claimed is:

1. A gas exchange analysis sensor head apparatus comprising:
    an active flow splitting device having a first output port and a second output port, the active flow splitting device configured to variably split an incoming gas flow between the first and second output ports;
    a sample chamber having an inlet and an outlet, the inlet coupled with the first output port of the active flow splitting device;
    a first gas analyzer coupled with the outlet of the sample chamber and configured to measure a concentration of a gas exiting the outlet of the sample chamber;
    a second gas analyzer coupled with the second output port of the active flow splitting device and configured to measure a concentration of said gas exiting the second output port of the active flow splitting device;
    a flow meter coupled between the first output port of the active flow splitting device and the inlet of the sample chamber the flow meter configured to measure a flow rate of gas entering the inlet of the sample chamber; and a feedback control circuit adapted to control the active flow splitting device to adjust the gas flow provided to the first output port responsive to a flow rate signal from the flow meter.

2. The apparatus of claim 1, wherein flow meter is coupled between the first output port of the active flow splitting device and the inlet of the sample chamber, the feedback control circuit controlling gas flow based on flow to the sample chamber.

3. The apparatus of claim 2, wherein measurements from the first and second gas analyzers are configured to be compared, thereby comparing gas analyzed from the sample chamber with excess gas diverted by the flow splitting device.

4. The apparatus of claim 2, wherein the feedback control circuit controls the active flow splitting device to adjust the gas flow provided to the first input port according to a user-selected flow rate.

5. The apparatus of claim 1, wherein the active flow splitting device includes a piezoelectric material.

6. The apparatus of claim 5, wherein the active flow splitting device comprises:
a piezoresistive actuator having a first end secured within the active flow splitting device and a second end located proximal to both the first and second output ports of the active flow splitting device; and
electrical contacts operatively coupled with the piezoresistive actuator, configured to apply a voltage to control a position of the second end relative to the first and second output ports and thereby control the flow ratio to the first and second output ports.

7. The apparatus of claim 6, wherein the actuator includes a metal strip coated on at least one side with a piezo-bender material.

8. The apparatus of claim 7, wherein the piezo-bender material comprises lithium tantalite.

9. The sensor head of claim 6, wherein an applied control potential controls the second end of the piezoresistive actuator to adjust the position of the second end relative to the first and second output ports such as to controllably adjust the gas flow provided to the first and second ports.

10. The apparatus of claim 1, wherein the active flow splitting device is located less than 12 inches from the sample chamber.

11. A gas exchange analysis sensor head apparatus comprising: A gas exchange analysis sensor head apparatus comprising:
an active flow splitting device having an input port, a first output port and a second output port, the active flow splitting device configured to controllably and variably split an incoming gas flow received at the input port to the first and second output ports;
a sample chamber having an inlet and an outlet, the inlet directly coupled with the first output port of the active flow splitting device;
a first gas analyzer coupled with the outlet of the sample chamber and configured to measure a concentration of a gas exiting the outlet of the sample chamber;
a second gas analyzer coupled with the second output port of the active flow splitting device and configured to measure a concentration of said gas exiting the second output port of the flow splitting device;
a flow meter directly coupled with and between the second output port of the active flow splitting device and the second gas analyzer, the flow meter configured to measure a flow rate of gas entering the second gas analyzer; and
a feedback control circuit adapted to control the active flow splitting device to adjust the gas flow provided to the second output port responsive to a flow rate signal from the flow meter.

12. The apparatus of claim 11, wherein the feedback signal controls the active flow splitting device to adjust the gas flow provided to the second output port or to the second output port according to a user-selected rate.

13. The apparatus of claim 11, wherein the active flow splitting device is located less than about 12 inches from the sample chamber.

* * * * *